United States Patent [19]

DeGraff

[11] Patent Number: 4,587,370
[45] Date of Patent: May 6, 1986

[54] AROMATIC HYDROCARBON ALKYLATION PROCESS PRODUCT RECOVERY METHOD

[75] Inventor: Richard R. DeGraff, Deerfield, Ill.

[73] Assignee: UOP Inc., Des Plaines, Ill.

[21] Appl. No.: 741,331

[22] Filed: Jun. 5, 1985

[51] Int. Cl.$^4$ ............................................. C07C 2/64
[52] U.S. Cl. ........................................ 585/450; 203/22; 203/23; 203/24; 203/26; 208/354; 208/355; 585/446; 585/466; 585/467
[58] Field of Search .................... 203/22, 23, 24, 25, 203/26; 585/450, 446, 466, 467; 208/354, 355

[56] References Cited

U.S. PATENT DOCUMENTS

| | | | |
|---|---|---|---|
| 2,787,648 | 4/1957 | King | 585/450 |
| 3,109,782 | 11/1963 | Nathan | 203/25 |
| 3,254,024 | 5/1966 | Huckins, Jr. et al. | 208/354 |
| 3,414,484 | 12/1968 | Carson et al. | 203/26 |
| 3,639,497 | 2/1972 | Martel et al. | 203/25 |
| 4,051,191 | 9/1977 | Ward | 260/671 R |
| 4,108,914 | 8/1978 | Gewartowski | 585/450 |
| 4,277,268 | 7/1981 | Spangler, Jr. | 203/24 |
| 4,360,405 | 11/1982 | Tsao | 203/24 |
| 4,395,310 | 7/1983 | Idenden | 203/26 |

FOREIGN PATENT DOCUMENTS

| | | | |
|---|---|---|---|
| 0131932 | 1/1985 | European Pat. Off. | 203/22 |
| 2823901 | 2/1979 | Fed. Rep. of Germany | 203/25 |

OTHER PUBLICATIONS

Canfield, R. C. et al., "Improving Cumene Yields Via Selective Catalysis," Process Technology, *Chemical Engineering*, Mar. 21, 1983, p. 32.

*Primary Examiner*—John Doll
*Assistant Examiner*—A. Pal
*Attorney, Agent, or Firm*—Thomas K. McBride; William H. Page, II; John F. Spears, Jr.

[57] ABSTRACT

A fractionation method is disclosed for the recovery of product alkylaromatic hydrocarbons produced by the alkylation of aromatic hydrocarbons. Three fractionation columns are employed in series. Aromatic feed hydrocarbons are recycled from the overhead of the first column, which is reboiled by the overhead vapor of the second column. The product alkylaromatic is recovered from the condensate produced in using the second column overhead as a heat source. The product alkylaromatic is also present in the bottoms of the second column which flows into a low pressure stripping column. The entire overhead vapor of the stripping column is compressed and passed into the lower portion of the second column.

17 Claims, 1 Drawing Figure

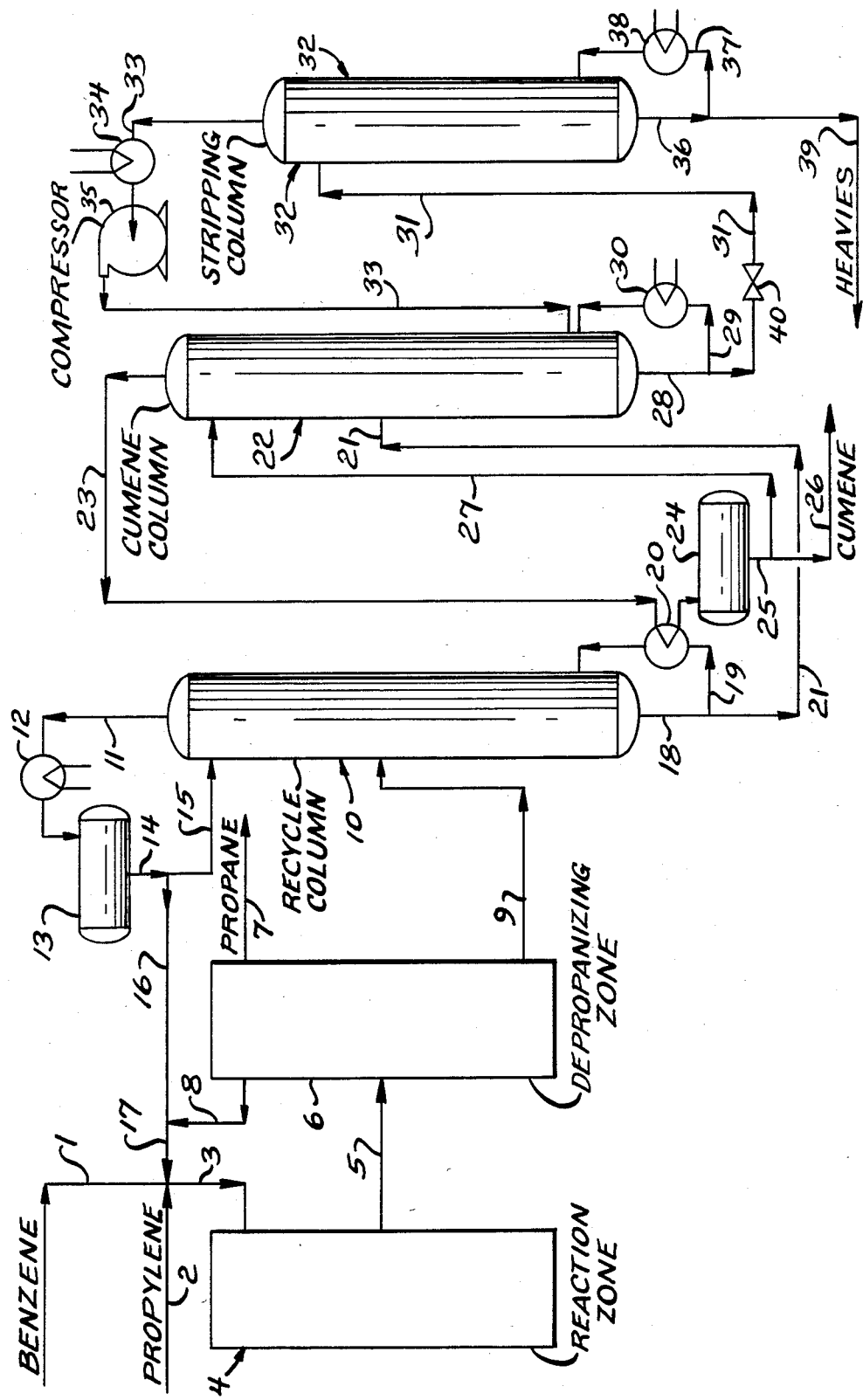

AROMATIC HYDROCARBON ALKYLATION PROCESS PRODUCT RECOVERY METHOD

FIELD OF THE INVENTION

The invention relates to a hydrocarbon conversion process. The invention more specifically relates to the production of alkylaromatic hydrocarbons by the reaction of an acrylic olefinic hydrocarbon with an aromatic feed hydrocarbon. The invention is directly related to the separatory method used to recover the product alkylaromatic hydrocarbons from the effluent of the alkylation reaction zone. This separatory method employs fractional distillation in three fractionation columns in series, with the subject invention being directly related to the method in which these columns are interconnected and the method in which they are reboiled.

PRIOR ART

The alkylation of aromatic hydrocarbons such as benzene using solid catalysts is a well-developed art which is practiced commercially in large scale industrial units. One commercial application of this process is the alkylation of benzene with propylene to form cumene (isopropylbenzene), which is subsequently used in the production of phenol and acetone. Those skilled in the art are therefore familiar with the general design and operation of such alkylation processes.

The prior art is well described in the literature. For instance, a typical flow scheme suitable for commercial use is depicted in U.S. Pat. No. 4,051,191 issued to D. J. Ward. This reference describes in some detail catalyst, reaction conditions, and separatory methods suitable for the recovery of cumene. The reactor effluent is passed into a rectification zone in which propane, charged to the process in admixture with the feed propylene, is separated for recycling and for rejection from the process. Liquid phase hydrocarbons recovered in the rectification zone are then passed into a two-column fractionation train comprising a recycle column and a cumene or product column. The benzene feed aromatic hydrocarbon is recycled from the top of the first fractionation column. The product cumene is recovered from the top of the second fractionation column, with heavy aromatic by-products being withdrawn from the bottom of the second column. A somewhat different product recovery fractionation train for commercial use is described in the article at page 32 of the Mar. 21, 1983 edition of *Chemical Engineering* magazine. This system employs four fractionation columns in series. The first fractionation column is a depropanizer column. The third column is a product column in which cumene is removed as the net overhead product. The net bottoms stream of the product column is passed into a recycle column with the overhead stream of this column apparently being recycled to the reaction zone. The alkylation process described in this article is based upon the use of an aluminum chloride catalyst system as compared to the solid phosphoric acid-type catalyst which is preferred in the previously cited reference.

It is known in the art of fractional distillation that the latent heat present in the overhead vapors of one fractionation column may be employed in the reboiler means of another fractionation column for the purpose of supplying heat to the other fractionation column. This is shown for instance in U.S. Pat. No. 3,254,024 issued to H. A. Huckins, Jr. et al. This reference is directed to the separation of close boiling $C_8$ aromatic hydrocarbons. The overhead vapor from a xylene splitter column is therefore used from this reference to reboil an ethylbenzene column. U.S. Pat. No. 4,360,405 issued to U. Tsao is pertinent for its showing a fractionation arrangement for use in the separation of close boiling mixtures in which the overhead vapor of one column is compressed and passed into a bottom portion of an immediately upstream fractionation column. The bottoms liquid from this upstream column flows into the top of the downstream column. This reference indicates this arrangement could be employed for the separation of close boiling hydrocarbons exemplified by the xylenes.

BRIEF SUMMARY OF THE INVENTION

The invention provides an improved method for the separation of the reactants and products of a process for the production of an alkylaromatic hydrocarbon by alkylation. The improvement basically relates to increased energy efficiency and elimination of the production of low pressure steam, which has only a small economic value in a typical petroleum refinery or petrochemical installation. The subject invention is characterized by the use of a relatively high pressure cumene or product column, with the overhead vapor of this stream being employed to reboil the immediately preceding recycle column. The invention is also characterized by the passage of a cumene rich bottoms stream from the cumene column to a relatively low pressure stripping column. The overhead vapor stream of the stripping column is rich in cumene and is compressed back into the cumene column. The subject invention is also an improvement in that the bottoms liquid pump normally employed on the bottoms stream of the cumene column is no longer required.

A broad embodiment of the invention may be characterized as a process for the production of an alkylaromatic hydrocarbon which comprises contacting a feed acyclic olefinic hydrocarbon and a feed aromatic hydrocarbon with an alkylation catalyst in an alkylation reaction zone maintained at alkylation-promoting conditions and producing a reaction zone effluent stream comprising the feed aromatic hydrocarbon, a product alkylaromatic hydrocarbon and high-boiling by-product hydrocarbons and subsequently recovering the product alkylaromatic hydrocarbon by a method which comprises the steps of passing a process stream comprising the feed aromatic hydrocarbon, the product alkylaromatic hydrocarbon and the by-product hydrocarbons into a recycle fractionation column operated at conditions which effect the separation of entering hydrocarbons into at least a net overhead stream, which is rich in the feed aromatic hydrocarbon, and a first bottoms stream, which comprises the product alkylaromatic hydrocarbon and the by-product hydrocarbons; passing the first bottoms stream into a product fractionation column operated at conditions effective to separate entering hydrocarbons into a first overhead vapor stream, which is rich in the product alkylaromatic hydrocarbon, and a second bottoms stream, which is also rich in the product alkylaromatic hydrocarbon and contains the by-product hydrocarbons; at least partially condensing the first overhead vapor stream in a reboiler means supplying heat to a lower portion of the recycle column, withdrawing a first portion of the resultant condensate from the process as a net product stream and returning a second portion of the condensate to the product column as reflux liquid; passing the second bottoms stream into a stripping column operated at fractional distillation conditions, including a pressure at least 15 psi lower than maintained in the product fractionation column, and effective to separate entering hydrocarbons into a second overhead vapor stream comprising the product alkylaromatic hydrocarbon and a third bottoms stream, which comprises the by-product hydrocarbons and is substantially free of the product alkylaromatic hydrocarbon; and compressing the second overhead vapor stream and then passing the second overhead vapor stream into the product fractionation column.

BRIEF DECRIPTION OF THE DRAWING

The drawing illustrates a preferred embodiment of the invention wherein product cumene is recovered from the overhead vapor of cumene column 22 by condensation of the overhead vapor in the reboiler 20 of the recycle column, with the cumene rich bottoms stream of the cumene column flowing through line 31 into the low pressure stripper 32. The high-boiling by-products leave through line 39 while the cumene is recycled by compression in means 35 to the cumene column.

DETAILED DESCRIPTION

The production of alkylaromatic hydrocarbons is an important industrial process. Although these hydrocarbons can be recovered from reaction products such as reformates or from natural occurring petroleum, the most commercially feasible route to the production of alkylaromatics appears to be the direct alkylation of a feed aromatic hydrocarbon with a feed acyclic olefinic hydrocarbon. A wide variety of alkylaromatic product hydrocarbons can be produced because of the various feed hydrocarbons in both the aromatic and acyclic categories which can be supplied to the alkylation zone. For instance, the feed aromatic hydrocarbon can be either benzene or toluene. The acyclic olefin can range from ethylene as in the production of ethyl benzene to a mixture of $C_{10}$ to $C_{15}$ acyclic olefins used in the alkylation processes designed to produce linear alkyl benzenes (LAB) destined for use as precursors in the production of detergents. The subject description will be basically couched in terms of the alkylation of benzene with propylene as this is the preferred embodiment of the invention. However, it is not thereby intended to preclude from the scope of the invention those other alkylation processes and hydrocarbon mixtures to which the subject invention is applicable.

In the traditional prior art fractionation method of recovering the product alkylaromatic hydrocarbon, the overhead streams of the fractionation columns has been condensed in water cooled heat exchangers resulting in the production of relatively low pressure steam. This is shown for instance in the previously cited article which illustrates the production of steam in the overhead system of all four fractionation columns. While this low pressure steam does contain a considerable amount of latent heat, it is typically at such a low temperature that the steam cannot be widely applied in the typical refinery. The low pressure steam generated in this manner therefore has little or no economic value. This results in all or most of the heat which is discharged in the overhead system of the column being unrecovered and being a net charge against the utility cost of operating the process. It is an objective of the subject invention to provide an improved fractional distillation type separation method for use in recovering the product of alkylation reaction zones. It is a specific objective of the subject invention to reduce the utility costs of operating the fractionation system used to recover a product alkylaromatic hydrocarbon made in an alkylation zone. It is another objective of the subject invention to minimize the capital cost of a low utility cost fractionation system.

In the subject invention, the product alkylaromatic hydrocarbon is recovered as the net overhead products of a relatively high pressure, as compared to the prior art, product column. The product column is the intermediate column of a three column fractionation train employed in the subject invention. The relatively high pressure maintained in the product column results in the overhead vapor of this column being sufficiently hot to reboil the preceding recycle column. The preceding column is referred to as the recycle column in reference to its traditional function of providing a relatively high-purity stream of unconverted feed aromatic hydrocarbon for recycling back to the reaction zone. The overhead product of the product column may therefore be of relatively high purity as the lighter hydrocarbons are removed upstream. For instance, it would normally contain greater than 99 mole percent cumene when cumene is being produced in the product. In the subject invention, the net bottoms stream removed from the product column will also be rich in the product alkylaromatic hydrocarbon and may have a concentration of the product hydrocarbon greater than 95 mole percent. The other components of the bottoms stream of the product column will comprise the high boiling by-products produced in the alkylation zone. These by-products are normally undesirable in the product alkylaromatic hydrocarbon, and they are therefore preferably withdrawn from the process as a separate stream. The by-products are produced by undesired oligomerization and alkylation reactions. For instance, in the production of cumene the high-boiling by-products would comprise propylene oligomers and diisopropylbenzene and possibly triisopropylbenzene.

It is normally desirable to minimize the temperature of that portion of the fractionation equipment in which these high boiling by-products are separated into the by-product stream which is removed from the process. Therefore, the desire to increase the overhead temperature of the product column is in conflict with the desire to minimize the temperature at the bottom of the product column when the high boiling by-products are withdrawn as a concentrated stream from the bottom of the product column. This conflict could be resolved by operating the product column at a relatively low pressure and employing a compressor to increase the temperature of the overhead vapor stream prior to its being used to reboil a recycle column. This is in the fashion of a traditional heat pump system. The overhead vapor stream of the product column is, however, normally a rather high volume vapor stream which would require a large and very expensive compressor and significant utilities for its operation.

In the subject process, the product rich bottoms stream of the product column is flashed into a relatively low pressure stripping column. This column is operated at a lower pressure than the product column. It is preferably operated at a pressure which is below about 25 psig. It is preferred that the product column is operated at a pressure at least 20 psi greater than the pressure maintained in the stripping column. The temperatures required at the bottom of the stripping column are therefore lower than the temperature which would be required in the bottom of the product column, which is operating at the increased pressure. The cumene rich overhead stream of the stripping column is now compressed into the product column. This overhead stream is much smaller than the overhead stream of the product column. It therefore can be compressed with a much smaller compressor than would be necessary to compress the overhead vapor stream of the product column. The utilities cost of operating this compressor are also greatly lower. It is also significant to point out that the pressure differential between the columns eliminates the need for a pump to transport the bottoms liquid of the product column into the stripping column.

The application of the subject invention to the typical alkylation zone may be discerned by reference to the drawing. In this representation of the preferred embodiment, the feed stream of benzene from line 1 is admixed with a propylene-propane feed stream from line 2. High-purity propylene could be charged to the process but the normal source of propylene will often contain significant amounts of propane. The propane passes through the process as an inert compound and does not interfere with the reaction. With the presently preferred SPA catalyst system, the presence of propane in the reaction zone is in fact desired and it is therefore partially recycled into the reaction zone from the downstream depropanizing zone. Recycle benzene and propane carried by line 17 are admixed with the feed hydrocarbons and the resultant hydrocarbon admixture is passed through line 3 into the reaction zone 4. The reactants are therein contacted with a suitable alkylation catalyst maintained at alkylation-promoting conditions. This effects the production of a reaction zone effluent stream carried by line 5 which comprises an admixture of unreacted benzene, propane, the product cumene and the high boiling by-product hydrocarbons formed in the reaction zone. The reactor effluent also contains hexenes and nonenes. The reaction zone effluent stream is passed into a depropanizing zone 6. The exact form of the depropanizing zone tends to vary between competing processes and different commercial installations. This zone can comprise a single depropanizing column or two rectified flash zones as shown in the prior art. This zone is preferably arranged to produce a net effluent stream of relatively high-purity propane withdrawn through line 7 to balance the net charge rate of propane to the process and a recycle stream transported through line 8 which will contain propane and possibly benzene. A normally liquid phase process stream is removed from the depropanizing zone in line 9 for passage into the fractionation train employed in the subject invention. This process stream will comprise benzene, cumene, and the by-product high-boiling or heavy hydrocarbons. This process stream is passed via line 9 into an intermediate point of the recycle column 10. The recycle column is operated at conditions which effect the separation of the entering hydrocarbons into an overhead vapor stream removed through line 11 and the bottoms stream removed in line 18. The overhead vapor stream should be essentially free of cumene and any heavier boiling hydrocarbons which enter the column. The overhead vapor stream passes through the overhead condenser 12 and then flows into the overhead receiver 13. The liquid phase benzene which thereby accumulates in the receiver is withdrawn through line 14 and divided into the recycle stream carried by line 16 and the reflux stream returned to the recycle column via line 15. Not shown on the drawing are the customary effluent streams associated with the upper portion of the recycle column. These two streams comprise a vapor off gas line for the overhead receiver and a drag benzene line which may be removed from the recycle column or from the overhead receiver liquid.

The net bottoms liquid from the recycle column carried by line 21 comprises the product cumene and the by-product heavy hydrocarbons. It should be essentially free of propane and benzene. The net bottoms stream is passed into the cument column 22 and is therein separated into a bottoms stream removed in line 28 and an overhead vapor stream removed through line 23. In accordance with the subject invention, the overhead vapor stream passes through the reboiler means 20 of the recycle column thereby supplying heat to the bottom of the recycle column. This results in at least a partial condensation and preferably a total condensation of the overhead vapor stream and the production of a condensate which is passed into the overhead receiver 24. This condensate liquid is high-purity cumene which is withdrawn through line 25 and divided into the reflux stream, returned to the cumene column through line 27 and the net product stream of the process which is removed through line 26. The heat given up by the overhead vapor stream in the reboiler vaporizes at least a portion of the bottom liquid circulating through line 19 to thereby provide vapors which pass into the bottom of the recycle column and effect the reboiling of the column.

The cumene column 22 is reboiled by means of heat supplied to the bottoms liquid circulating through line 29 and partially vaporized in reboiler means 30. The net bottoms stream removed from the cumene column in line 31 is passed through pressure reducing valve 40 into an upper portion of the stripping column 32. This column is operated at fractionation conditions which are effective to separate the entering hydrocarbons into the overhead vapor stream withdrawn through line 33 and the bottoms liquid withdrawn through line 36. The bottoms liquid of line 36 should be rich in the heavy hydrocarbon by-products of the alkylation reaction. A portion of the bottoms liquid is circulated through line 37 and the reboiler means 38 which receives heat from an external source such as high pressure steam or hot oil. The high boiling by-products for the alkylation reaction are therefore concentrated into a relatively small net bottoms stream discharged from the process through line 39. The overhead vapor stream of line 33 has a high concentration (greater than 90 mole percent) of cumene. The overhead vapor stream is preferably heated in the heating means 34 and is then compressed in means 35. The cumene rich overhead vapor stream then continues through line 33 and is preferably passed into the cumene column at a lower point near or below the lowest most tray within this column. The overhead vapor stream could, however, be passed into the column at higher points if so desired.

The subject invention is practiced with a reaction zone containing a solid catalyst. Preferably, the catalyst is one commonly referred to as an SPA catalyst. Suitable SPA catalysts are available commercially. As used herein the term "SPA catalyst" or its equivalent is intended to refer generically to a solid catalyst which contains as one of its principal raw ingredients an acid of phosphorus such as ortho-, pyro- or tetra-phosphoric acid. These catalysts are normally formed by mixing the acid with a siliceous solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives such as mineral talc, fullers earth and iron compounds including iron oxide have been added to the carrier to increase its strength and hardness. The combination of the carrier and the additives normally comprises about 15-30 wt. % of the catalyst, with the remainder being the phosphoric acid. However, the amount of phosphoric acid used in the manufacture of the catalyst may vary from about 8-80 wt. % of the catalyst as described in U.S. Pat. No. 3,402,130. The amount of the additive may be equal to about 3-20 wt. % of the total carrier material. Further details as to the composition and production of typical SPA catalysts may be obtained from U.S. Pat. Nos. 3,050,472; 3,050,473 and 3,132,109 and from other references.

The subject invention is not restricted to use with a SPA type catalyst. For instance the previously cited article describes the use of $AlCl_3$ catalysts and indicates this is a commonly used catalyst in the production of ethyl benzene. In addition, the patent literature describes a vast array of zeolite alkylation catalysts and processes for their use. It is therefore contemplated to practice the subject invention using a catalyst comprising an amorphous or a crystalline alumino silicate such as a "ZSM-5" zeolite. Due to the nature of the aluminosilicates they are normally not used in the pure form but are composited into a porous support matrix in combination with an alumina or silica or clay. The alkylation reactions with these materials have been decribed as being both vapor-phase and liquid-phase processes. The reaction conditions for use with differing catalysts, which are set out in the references, will vary from the preferred conditions set out herein for use in conjunction with SPA-type catalysts. Further information on zeolitic alkylation catalysts may be obtained from a number of sources including U.S. Pat. Nos. 3,755,483; 4,300,011; 4,469,908 and 4,489,214.

The reaction zone is maintained at alkylation-promoting conditions. As previously stated the conditions must be adjusted to compensate for the specific catalyst being employed and the reactants being charged to the process. In the case of an SPA type catalyst these conditions include a pressure of about 300 to 1000 psig and a temperature of about 300° to 600° F. The liquid hourly space velocity of reactants may range from about 0.5 to 2.5. It is preferred that an excess of the aromatic hydrocarbon be present in the reaction zone. The mole ratio of the aromatic hydrocarbon to the olefin should be within the broad range of 3:1 to 20:1. A ratio of about 8:1 is preferred for the production of cumene. It is preferred that the reactant stream be mixed-phase through the reactor. The feed stream therefore preferably contains some unreactive light paraffins having the same number of carbon atoms per molecule as the olefin. In the production of cumene it is preferred that the amount of propane in the reaction zone feed stream be at least equal to the amount of propylene in this stream. This may be accomplished by using a dilute propylene feed stream or by recycling propane. The previously cited article indicates representative conditions for the use of an $AlCl_3$ catalyst system include a temperature below 275° F. and a pressure of less than 50 psig.

The preferred embodiment of the invention may accordingly be described as a process for the production of an alkylaromatic hydrocarbon which comprises contacting a feed acyclic olefinic hydrocarbon and a feed aromatic hydrocarbon with a solid alkylation catalyst in an alkylation reaction zone maintained at alkylation-promoting conditions and producing a reaction zone effluent stream comprising the feed aromatic hydrocarbon, a monoalkylaromatic product hydrocarbon and high-boiling by-product hydrocarbons and subsequently recovering the product alkylaromatic hydrocarbon by a method which comprises the steps of passing a process stream comprising the feed aromatic hydrocarbon, the monoalkylaromatic product hydrocarbon and the by-product hydrocarbons into a recycle fractionation column operated at conditions which effect the separation of entering hydrocarbons into at least a net overhead stream, which is rich in the feed aromatic hydrocarbon, and a first bottoms stream, which comprises the product hydrocarbon and the by-product hydrocarbons; passing the first bottoms stream into a product fractionation column operated at conditions effective to separate entering hydrocarbons into a first overhead vapor stream, which is rich in the product hydrocarbon and substantially free of the by-product hydrocarbons, and a second bottoms stream, which is rich in the product hydrocarbon and also comprises the by-product hydrocarbons; at least partially condensing the first overhead vapor stream in a reboiler means supplying heat to the bottom portion of the recycle column, withdrawing a first portion of the resultant condensate from the process as a net product stream and returning a second portion of the condensate to the product column as reflux liquid; passing the second bottoms stream into a stripping column operated at fractional distillation conditions, including a pressure which is at least 20 psi lower than is maintained in the product fractionation column, effective to separate entering hydrocarbons into a second overhead vapor stream comprising the product alkylaromatic hydrocarbon and a third bottoms stream, which comprises the by-product hydrocarbons and is substantially free of the product hydrocarbon; and compressing the second overhead vapor stream and then passing the second overhead vapor stream into a bottom portion of the product fractionation column. As used herein the term substantially free is intended to indicate a molar concentration of the indicated substance less than about 2 and preferably less than 1 percent. The term "rich" is intended to indicate a concentration of the specified compound or class of compounds exceeding about 75 mole percent.

I claim as my invention:

1. A process for the production of an alkylaromatic hydrocarbon which comprises contacting a feed acyclic olefinic hydrocarbon and a feed aromatic hydrocarbon with an alkylation catalyst in an alkylation reaction zone maintained at alkylation-promoting conditions and producing a reaction zone effluent stream comprising the feed aromatic hydrocarbon, a product alkylaromatic hydrocarbon and high-boiling by-product hydrocarbons and subsequently recovering the product alkylaromatic hydrocarbon by a method which comprises the steps of:

(a) passing a process stream comprising the feed aromatic hydrocarbon, the product alkylaromatic hydrocarbon and the by-product hydrocarbons into a recycle fractionation column operated at conditions which effect the separation of entering hydrocarbons into at least a net overhead stream, which is rich in the feed aromatic hydrocarbon, and a first bottoms stream, which comprises the product alkylaromatic hydrocarbon and the by-product hydrocarbons;

(b) passing the first bottoms stream into a product fractionation column operated at conditions effective to separate entering hydrocarbons into a first overhead vapor stream, which is rich in the product alkylaromatic hydrocarbon, and a second bottoms stream, which is rich in the product alkylaromatic hydrocarbon and also comprises the by-product hydrocarbons;

(c) at least partially condensing the first overhead vapor stream in a reboiler means supplying heat to a lower portion of the recycle column, withdrawing a first portion of the resultant condensate from the process as a net product stream and returning a second portion of the condensate to the product column as reflux liquid;

(d) passing the second bottoms stream into a stripping column operated at fractional distillation conditions, including a lower pressure than is maintained in the product fractionation column, and effective to separate entering hydrocarbons into a second overhead vapor stream comprising the product alkylaromatic hydrocarbon and a third bottoms stream, which comprises the by-product hydrocarbons and is substantially free of the product alkylaromatic hydrocarbon; and, (e) compressing the second overhead vapor stream and then passing the second overhead vapor stream into the product fractionation column.

2. The process of claim 1 further characterized in that the stripping column is operated at a pressure at least 15 psi lower than the pressure at which the product fractionation column is operated.

3. The process of claim 2 further characterized in that the second overhead vapor stream is passed into a lower portion of the product fractionation column.

4. The process of claim 1 further characterized in that the feed aromatic hydrocarbon is toluene.

5. The process of claim 4 further characterized in that the feed acyclic olefinic hydrocarbon is a $C_3$ to $C_5$ hydrocarbon.

6. The process of claim 5 further characterized in that the feed acyclic olefinic hydrocarbon is propylene.

7. The process of claim 1 further characterized in that the feed aromatic hydrocarbon is benzene.

8. The process of claim 7 further characterized in that the feed acyclic olefinic hydrocarbon is propylene.

9. The process of claim 7 further characterized in that the product alkylaromatic hydrocarbon is a bialkylaromatic hydrocarbon.

10. The process of claim 1 further characterized in that the alkylation catalyst comprises a crystalline aluminosilicate.

11. The process of claim 1 further characterized in that the alkylation catalyst is a solid phosphoric acid type catalyst.

12. A process for the production of an alkylaromatic hydrocarbon which comprises contacting a feed acyclic olefinic hydrocarbon and a feed aromatic hydrocarbon with a solid alkylation catalyst in an alkylation reaction zone maintained at alkylation-promoting conditions and producing a reaction zone effluent stream comprising the feed aromatic hydrocarbon, a monoalkylaromatic product hydrocarbon and high-boiling by-product hydrocarbons and subsequently recovering the product alkylaromatic hydrocarbon by a method which comprises the steps of:

(a) passing a process stream comprising the feed aromatic hydrocarbon, the monoalkylaromatic product hydrocarbon and the by-product hydrocarbons into a recycle fractionation column operated at conditions which effect the separation of entering hydrocarbons into at least a net overhead stream, which is rich in the feed aromatic hydrocarbon, and a first bottoms stream, which comprises the product hydrocarbon and the by-product hydrocarbons;

(b) passing the first bottoms stream into a product fractionation column operated at conditions effective to separate entering hydrocarbons into a first overhead vapor stream, which is rich in the product hydrocarbon and substantially free of the by-product hydrocarbons, and a second bottoms stream, which is rich in the product hydrocarbon and also comprises the by-product hydrocarbons;

(c) at least partially condensing the first overhead vapor stream in a reboiler means supplying heat to the bottom portion of the recycle column, withdrawing a first portion of the resultant condensate from the process as a net product stream and returning a second portion of the condensate to the product column as reflux liquid;

(d) passing the second bottoms stream into a stripping column operated at fractional distillation conditions, including a pressure which is at least 20 psi lower than is maintained in the product fractionation column, and effective to separate entering hydrocarbons into a second overhead vapor stream comprising the product alkylaromatic hydrocarbon and a third bottoms stream, which comprises the by-product hydrocarbons and is substantially free of the product hydrocarbon; and, (e) compressing the second overhead vapor stream and then passing the second overhead vapor stream into a bottom portion of the product fractionation column.

13. The process of claim 12 further characterized in that the feed aromatic hydrocarbon is benzene.

14. The process of claim 13 further characterized in that the feed acyclic olefinic hydrocarbon is a $C_3$ to $C_5$ hydrocarbon.

15. The process of claim 14 further characterized in that the feed acyclic olefinic hydrocarbon is propylene.

16. The process of claim 12 further characterized in that the alkylation catalyst comprises a crystalline aluminosilicate.

17. The process of claim 12 further characterized in that the alkylation catalyst is a solid phosphoric acid type catalyst.

* * * * *